United States Patent

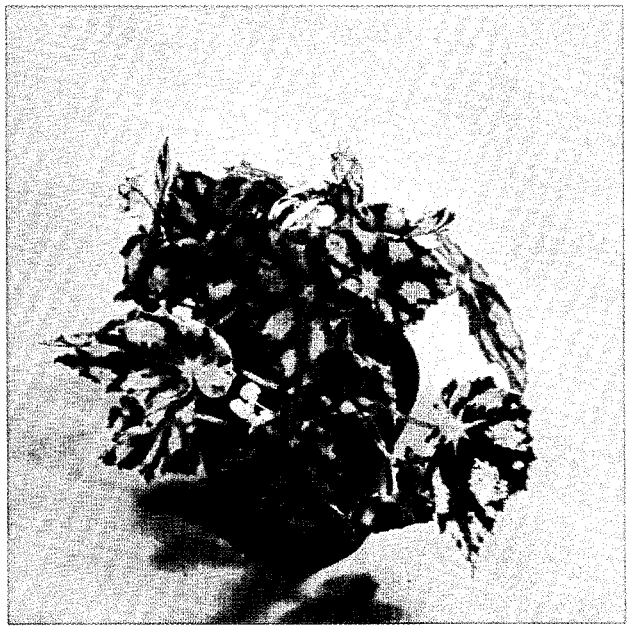

Plant Pat. 3,968
Patented Oct. 26, 1976

3,968

BEGONIA PLANT

Leslie Woodriff, McKinleyville, Calif., assignor to Mikkelsens, Inc., Ashtabula, Ohio Filed Sept. 5, 1975, Ser. No. 610,776
Int. Cl.[2] A01H 5/00
U.S. Cl. Plt.—68 1 Claim The present invention relates to a distinct rhizomatous begonia cultivar, hereinafter referred to by the cultivar name Tiger Kitten.

Tiger Kitten was originated by me through a controlled breeding program in McKinleyville, Calif. The female parent was B. Cleopatra (unpatented) and the male parent was *B. boweri* Nigramarga (unpatented). Asexual reproduction of Tiger Kitten was accomplished in McKinleyville, Calif. by taking leaf cuttings from the new cultivar. Such asexual reproduction has demonstrated that the unique characteristics of the new cultivar are firmly fixed and retained through successive propagations.

The following characteristics in combination distinguish Tiger Kitten from both its parents and other begonias of this type commercially known and used in the floriculture industry:

1. Leaf cuttings root and develop adventitious shoots in approximately six to seven weeks, which is seven to ten days faster than *B. boweri* Nigramarga.
2. Bright green leaves with dark brown to dark green veinal mottling has greater color contrast than leaves of *B. boweri* Nigramarga when produced under the same environment.
3. Hairy margins of leaves are distinctive.
4. Growth regulators such as Cycocel inhibit leaf petiole elongation so that a massive leaf clump can be maintained under high light and high temperature conditions.
5. Plants grown in plastic covered houses rather than in glass houses change color of foliage from bright dark green to yellow green; mottling becomes chocolate brown.
6. The cultivar is a dwarf compact plant very capable of existing for several weeks under conditions of water and nutrient stress. Thus this begonia is ideal for terrariums, and miniature combination plantings, and mass marketing.
7. Leaf production at any given time is much greater than the usual begonias in the dwarf types, and is 20% to 30% more than *B. boweri* Nigramarga.
8. Leaves are smaller and more numerous than the seed parent B. Cleopatra. My new cultivar is very adaptable to production in 2, 3 or 4 inch pots or 6 inch hanging baskets. The abundance of leaves is of commercial importance to propagators and producers of finished plants.
9. Total plant appearance has more eye appeal or attractiveness than either B. Cleopatra or *B. boweri* Nigramarga.

The accompanying colored photographic drawing illustrates the overal appearance of the new cultivar when grown in a 3 inch pot, with the colors being as true as it is reasonably possible to obtain in a colored reproduction of this type.

The following is a detailed description of my new begonia variety based on plants produced under commercial practices in McKinleyville, Calif. Color references are made to the Royal Horticultural Society Colour Chart except where general color terms of ordinary dictionary significance are used.

*Parentage:* Controlled pollination of B. Cleopatra × *B. boweri* Nigramarga.

*Propagation:* By leaf cuttings 1–1½ inches in diameter with ½ inch petiole; when stuck in appropriate propagating media at 68°–70° cuttings will root in 14–20 days and develop adventitious shoots in an additional 21–28 days for a total of 36 to 48 days propagating time.

*Rooting Habit:* Very profuse; fine dendritic roots, quite rapid.

*Plant Form:* Compact and dwarf developing from underground rhizomatous growth. All leaves and flowers arise from the underground rhizome. Young plants two or three months after propagation seldom exceed 3 to 4 inches in height or 6 inches in diameter.

*Habit of Growth:* Sprawling, slow, rhizomatous growth.

*Blooming Habits:* Flowers arise directly from the rhizome as do the leaves. The flowering stems elongate two to four inches above the canopy of leaves and are arranged on a panicle.

*Blooming Season:* In the area of McKinleyville, Calif. the blooming season is during the spring months of March and April, with occasional flowering continuing into May.

*Foliage:* Firm, well textured and extremely durable under adverse growing conditions for begonias. Leaves are very abundant for a rhizomatous type begonia, indicating a rapid growth of the rhizome itself.

*Size*—Generally mature leaves measure two inches wide by three inches long. Leaf petioles are heavily flecked with red out of which arises a transparent follicle.

*Shape*—Cordate, veins are palmate.

*Texture*—Top surface smooth, glabrous, with iridescent sheen.

*Margin*—Toothed, with upright hairy appendages around the entire margin.

*Color — Young leaves:* top interveinal 146C–D; around veins, brown; underside interveinal near 145A; around veins, red toward 53B.

*Mature leaves:* top interveinal, green 146B; around veins, darker than 147A; underside interveinal, green nearly 146D, around veins, toward red 53B. Environmental conditions conditions can greatly alter the color tones.

*Disease Resistance:* When grown with other begonias infected with mildew and *Xanthomonas begoniae*, this cultivar does not become infected with either of these common diseases of begonias.

FLOWERS

*Borne*—On stems of comparable diameter to the leaf petioles, namely 1.5 mm. to 2.5 mm.; stems are flecked with red and emerging follicles, and arise directly out of the rhizome with flowers arranged in a panicle.

*Quantity*—Flowering is 25% more profuse than either parent and similar types of begonias; both male and female flowers are prevalent.

*Buds*—Unopened flower buds are approximately 5 to 6 mm. in diameter.

*Petals*—White with very light tinge of pink and are two in number.

*Stamens*—Light yellow.

*Pollen*—Whitish yellow.

*Styles/Ovaries*—Light yellow—three stigmas and, as normal, three ovaries.

I claim:

1. A new and distinct cultivar of begonia plant known by the cultivar name Tiger Kitten and particularly characterized as to uniqueness by the combined characteristics of relatively fast rooting habit; bright green leaves with dark brown to dark green veinal mottling and hairy leaf margins; favorable susceptibility to growth regulators so as to achieve a massive leaf clump which can be maintained under high light and high temperature conditions;

variable foliage color depending upon growth in plastic covered or glass greenhouses; dwarf, compact growth habit which renders plant capable of existing for several weeks under conditions of water and nutrient stress; superior leaf production; and attractive total plant appearance.

No references cited.

ROBERT E. BAGWILL, Primary Examiner